(12) United States Patent
Marin

(10) Patent No.: US 7,872,008 B2
(45) Date of Patent: *Jan. 18, 2011

(54) METHOD FOR TREATING INSULIN RESISTANCE, ABDOMINAL OBESITY, HYPERTENSION, HYPERINSULINEMIA, AND ELEVATED BLOOD LIPIDS WITH A CORTISOL INHIBITOR

(75) Inventor: Per Marin, Güteborg (SE)

(73) Assignee: Cortendo AB, Gothenburg (SE)

( * ) Notice: Subject to any disclaimer, the term of this patent is extended or adjusted under 35 U.S.C. 154(b) by 629 days.

This patent is subject to a terminal disclaimer.

(21) Appl. No.: 10/654,809

(22) Filed: Sep. 4, 2003

(65) Prior Publication Data

US 2004/0077660 A1   Apr. 22, 2004

Related U.S. Application Data

(60) Division of application No. 09/712,472, filed on Nov. 14, 2000, now Pat. No. 6,642,236, which is a division of application No. 09/211,282, filed on Dec. 14, 1998, now Pat. No. 6,166,017, which is a continuation of application No. 08/776,983, filed on Feb. 6, 1997, now Pat. No. 5,849,740, and a continuation of application No. PCT/SE94/00729, filed on Aug. 9, 1994.

(51) Int. Cl.
*A61K 31/50* (2006.01)

(52) U.S. Cl. ..................... 514/247

(58) Field of Classification Search .......... 514/247, 514/178, 396, 467, 909, 254.07
See application file for complete search history.

(56) References Cited

U.S. PATENT DOCUMENTS

| | | | | |
|---|---|---|---|---|
| 4,466,978 | A * | 8/1984 | Naylor | 514/474 |
| 4,491,588 | A | 1/1985 | Rosenburg et al. | |
| 4,814,333 | A | 3/1989 | Ravaris | |
| 4,871,741 | A | 10/1989 | Gadebusch et al. | |
| 4,956,391 | A * | 9/1990 | Sapse | 514/391 |
| 5,175,144 | A | 12/1992 | Walser | |
| 5,432,176 | A | 7/1995 | Walser | |
| 5,527,788 | A * | 6/1996 | Svec et al. | 514/169 |
| 5,591,736 | A | 1/1997 | Walser | |
| 5,849,740 | A * | 12/1998 | Marin | 514/247 |
| 6,040,307 | A | 3/2000 | Gray et al. | |
| 6,166,017 | A * | 12/2000 | Marin | 514/247 |
| 6,428,809 | B1 | 8/2002 | Abrams et al. | |
| 6,545,028 | B2 | 4/2003 | Jensen et al. | |
| 6,642,236 | B1 * | 11/2003 | Marin | 514/247 |
| 6,702,683 | B2 | 3/2004 | Abrams et al. | |
| 6,846,800 | B1 | 1/2005 | Johannsson et al. | |

OTHER PUBLICATIONS

Phillips et al. Antimicrobial Agents and Chemotherapy, 1987, vol. 31, No. 4, pp. 647-649.*
Miettinen, T.A. Journal of Lipid Research, 1988, vol. 29, pp. 43-51.*
Peeke et al. Ann. N. Y. Acad. Sci., 1995, vol. 771, pp. 665-676 (Abstract attached).*
Viscera Obesity: A "Civilization Syndrome". Obesity Research, vol. 1 No. 3, May 1993.
A.T. Sapse, "Stress, Cortisol, Interferon and 'Stress' Diseases—I. Cortisol as the Cause of 'Stress' Diseases". Medical Hypotheses, vol. 13 pp. 31-44, 1984.
Pepper, G.M. et al, "Ketoconazole Reversed Hyperandrogenism . . . ," J. Clin. Endocrin. & Metab., 1987, vol. 65, No. 5, pp. 1047-1052.
Verhelst, J.A. et al., "Use of Ketoconazole in the Treatment of Virilizing Adrenocortical Carcinoma," ACTA Endocrin., 1989, vol. 121, No. 2, pp. 229-234.
Sonino, N., et al., "Ketoconazole treatment in Cushing's syndrome . . . ," Clin. Endocrin. 1991 United Kingdom, 1991, vol. 35, No. 4, pp. 347-352.
Krishnaiah, Y.S.R., et al., "Drug Interaction of tolbutamide with ketoconazole in diabetic rabbits," Indian J. Pharmacol., 1993, vol. 125, No. 3, pp. 146-148.
Brindley, D.N., et al., "Neuroendocrine regulation and obesity," Int'l J. Obesity 1992 United Kingdom, 1992, vol. 16, No. Suppl. 3, pp. S73-S79.
European Patent Office, European Search Report in respect of EP 03 01 2414, Aug. 4, 2003.
Bjorntorp, P., "Metabolic implications of body fat distribution," Diabetes Care 1991, 14(12):1132-1143.
Bjorntorp, P., "Regional fat distribution—implications for type II diabetes," Int J Obesity 1992, 16(4):S19-S27.
Brindley, D.N., "Role of glucocorticoids and fatty acids in the impairment of lipid metabolism," Int J Obesity 1995, 19(1):S69-S75.
Byrd et al., "Paecilomyces varioti pneumonia in a patient with Diabetes Mellitus," J. Diab Comp 1992, 6:150-153.
Nichols, R., "Problems associated with medical therapy of Canine Hyperandrenocorticism," Problems in Veterinary Medicine, 1990, 2(4):551-556.
Peeke and Chrousos, "Hypercortisolism and obesity," Ann. New York Acad. Sci. 665-676.
Rotstein et al., "Stereoisomers of ketoconazole: Preparation and biological activity," J Med Chem 1992, 35:2818-2825.

(Continued)

*Primary Examiner*—James D Anderson
(74) *Attorney, Agent, or Firm*—Bradley N. Ruben

(57) ABSTRACT

The invention concerns the use of ketoconazole and derivatives having a corresponding biological activity, and combinations thereof, in the treatment of abdominal obesity, hypertension, hyperinsulinemia, and elevated blood lipids.

3 Claims, No Drawings

OTHER PUBLICATIONS

Balbi, C. et al., "Treatment with Ketoconazole in Diabetic Patients with Vaginal Candidiasis," Drugs Exptl. Clin. Res., XII(5), 413-414 (1986).

National Institutes of Health, "Cushing's Syndrome," Pub. No. 08-3007, Jul. 2008, via http://endocrine.niddk.nih.gov/pubs/cushings/cushings.htm.

Paterson et al., "Metabolic syndrome without obesity" Proc. Nat. Acad. Sci., 2004, vol. 101. No. 18, pp. 7088-7093.

Paola Loli et al., "Use of Ketonconazole in the Treatment of Cushing's Syndrome," J. Clin. Endocrinology and Metabolism, vol. 63, No. 6, 1365-1371.

\* cited by examiner

METHOD FOR TREATING INSULIN RESISTANCE, ABDOMINAL OBESITY, HYPERTENSION, HYPERINSULINEMIA, AND ELEVATED BLOOD LIPIDS WITH A CORTISOL INHIBITOR

This application is divisional of application Ser. No. 09/712,472, filed Nov. 14, 2000 now U.S. Pat. No. 6,642,236, which is a divisional of application Ser. No. 09/211,282, filed Dec. 14, 1998, now U.S. Pat. No. 6,166,017, which is a continuation of application Ser. No. 08/776,983, filed Feb. 6, 1997, now U.S. Pat. No. 5,849,740, and a continuation of PCT/SE94/00729, filed Aug. 9, 1994.

The present invention relates to the use of ketoconazole or molecules resembling ketoconazole but with some side-chains, not affecting the biological activity compared to ketoconazole, changed for manufacturing drugs for treatment of diabetes mellitus type II.

The drug ketoconazole (e.g., under the Fungoral™ brand) is a well-documented drug for treatment of fungal infections. The process of making ketoconazole is well known and described. In this invention Fungoral™ capsules aimed at oral administration should be used. This means that Fungoral™ should be administered the same way (oral) and in the same composition that is already well-known on the market for treatment of fungal infections the oral route. Therefor it is not considered necessary to further describe the process of making Fungoral™. For the same reason it is not considered necessary to give a full, clear, concise and exact term of this drug, since it is already well known for persons skilled in the art of medicine.

The drug comprising ketoconazole (e.g., under the Fungoral™ brand) and chemically closely related substances, the mode of operation of which is to influence the normal cortisol synthesis in the adrenal glands in such a way that the production of biologically perfectly acting cortisol is partly inhibited, is intended to be used for medical treatment of diabetes mellitus type II in men and women as well as for counteracting the risk factors which are parts of the Metabolic Syndrome (also known as "the deadly quartet" or "Syndrome X" or the "Insulin Resistance Syndrome"), which is characterised by an accumulation of risk factors for cardiovascular disease, stroke and diabetes mellitus type II, i.e. insulin resistance, hyperinsulinemia, abdominal obesity, (caused by an accumulation of intra-abdominal fat), elevated serum lipids, and raised blood pressure, as well as reducing the risk of development of these diseases.

In this new invention ketoconazole shall be administered the oral route in doses of 100-800 mg daily. The drug can be administered once or several times daily. At present a dose of 400 mg administered in the evening has been proven to be the best mode. However, we also claim that administration at other points of time, and in other doses (100-800 mg) can be equally effective.

Since ketoconazole is also inhibiting the normal production of testosterone in men, it is possible that this sex needs a certain amount of testosterone supplementation when treated with ketoconazole, to have an optimal effect of the treatment.

We have investigated a group of people with diabetes mellitus type II. They have been treated with ketoconazole during 2 and 6 weeks, respectively. Investigations before and after treatment have shown a decrease in blood glucose measured either in the fasting state or at 2 hours after an intravenous glucose infusion, and most important, a remarkable improvement of insulin sensitivity. More exact data from these studies are given in the tests described below.

Since a decreased insulin sensitivity is a central part of "The metabolic syndrome", also known as "The deadly quartet", "Syndrome X" or the "Insulin Resistance Syndrome" we also claim that fungoral treatment to people with risk factors according to this syndrome should be expected to be effective also for treatment of these specific risk factors (abdominal obesity, hypertension, elevated blood lipids) as well as for decreasing the risk for diseases caused by these risk factors (Cardiovascular disease such as coronary artery disease, other arteriosclerotic manifestations including stroke).

The mechanism of the action of ketoconazole is that the substance influence the cortisol synthesis of the adrenal glands in such a way that a sub-fraction of a biologically non-perfect substance similar to cortisol, so called "crippled cortisol", is formed instead of the normal cortisol molecule.

The cortisol antagonistic effect of the drug is considered to have a central importance for the positive effects on the risk factors mentioned above, decreasing the metabolic activity of fat inside the abdominal cavity, which in turn leads to a decreased fat infiltration of the liver, improving the glucose homeostasis over the liver and peripherally in the tissues in turn leading to improvement of diabetes mellitus type II (decreasing blood glucose and increasing insulin sensitivity), reducing the serum lipids through improvement of the regulating mechanisms in the liver and also inhibiting cholesterol synthesis by a direct effect on the adrenal glands. A positive effect on the blood pressure can also be expected via the cortisol-antagonistic effect.

The scientific basis for these effects can be explained by an inhibition of the physiologically increased cortisol secretion rate that is known to be present under the conditions described above. (The metabolic syndrome and its synonyms described above). This increased cortisol secretion can per se explain all the parts of the syndrome described including the development of diabetes mellitus type II. The scientific explanation for the beneficial effects of ketoconazole on the treatment of diabetes mellitus type II is its effects of decreasing the secretion of biologically active cortisol.

The basic substance is ketoconazole in the chemical form which is known and well documented in the literature. This substance can be further chemically modified while maintaining the same biological effects by exchange of different molecular side chains. These substances similar to ketoconazole can then be expected to have similar and/or better effects on the cortisol inhibiting mechanism, which is described above.

A positive effect on the treatment of patients with diabetes mellitus type II with ketoconazole has been shown in that after the administration of ketoconazole a reduction of the insulin insensitivity (resistance), which is often associated with this disease, has been measured. This has been measured as an improved (i.e., reduced) insulin resistance measured with a so called euglychemic glucose clamp method. Thus, the examined patients have improved with regard to their diabetes, measured in the above described way, which in parallell also have resulted in lower blood glucose after treatment compared to before treatment.

The category of patients, that would have an especially good use of ketoconazole are patients with diabetes mellitus type II with insulin insensitivity and despite treatment with usual anti-diabetic drugs and/or insulin still have remaining elevated glucose values in the blood in fasting condition as well as after a meal. The investigated patients had decreased insulin sensitivity compared to healthy persons, measured by euglychemic glucose clamp. Supply of ketoconazole to this category of patients has been shown to have a positive and specific effect on the insulin insensitivity in such a way that their diabetes mellitus type II was improved. This was measured as improved insulin sensitivity and lower blood glucose.

Other positive effects have also been detected among these patients: Reduced cholesterol levels in the plasma as well as decreasing blood pressure values.

Results of Clinical tests of women with diabetes mellitus type II, treated with ketoconazole.

Group 1 consists of 3 patients (mean age: 46 years) treated with ketoconazole for 2 weeks, administered orally 22:00 in the evening in the dose of 400 mg.

Group 2 consists of 5 patients (mean age: 51 years) treated with ketoconazole for 6 weeks, administered orally 22:00 in the evening in the dose of 400 mg. Results are expressed as mean values within groups.

| Variables studied | Group 1 | | Group 2 | |
| --- | --- | --- | --- | --- |
| | Before t. | After t. | Before t. | After t. |
| Fasting blood glucose (mmol/L) | 10.20 | 8.77 | 7.20 | 7.10 |
| Blood glucose (mmol/L) 2 hours after start of an i.v. glucose in-fusion | 9.73 | 7.90 | 6.48 | 5.76 |
| GIR (glucose in-fusion rate during euglycemic glucose clamp expressed as mg glucose per minute divided by lean body mass), indicating insulin sensitivity | 0.9 | 1.85 | 2.97 | 4.32 |
| Fasting serum total cholesterol (mmol/L) | 5.80 | 5.67 | 4.80 | 4.10 |
| Systolic blood pressure (mm Hg) measured after 5 min. in supine position. 2 measurements averaged | 140 | 135 | 125 | 123 |
| Diastolic blood pressure (mm Hg) measured after 5 min. in supine position. 2 measurements averaged | 70 | 70 | 75 | 72 |
| Serum-ASAT (µkat/L) | 0.36 | 0.33 | 0.26 | 0.25 |
| Serum-ALAT (µkat/L) | 0.61 | 0.52 | 0.40 | 0.37 |

What is claimed is:

1. A method for the medical treatment of a condition selected from the group consisting of insulin resistance, abdominal obesity, hypertension, hyperinsulinemia, and elevated blood lipids in a patient with Metabolic syndrome, which method comprises the steps of:
   providing ketoconazole; and
   administering to said patient with Metabolic syndrome in need thereof an amount of said ketoconazole effective to treat said condition.

2. The method according to claim 1, wherein the daily dose of ketoconazole is between 100 and 800 mg.

3. The method according to claim 2, wherein 400 mg of said ketoconazole is administered to the patient in the evening.

* * * * *